(12) United States Patent
Rao et al.

(10) Patent No.: US 6,720,158 B2
(45) Date of Patent: *Apr. 13, 2004

(54) SPLICE VARIANTS OF BRCA1

(75) Inventors: Veena N. Rao, Collegeville, PA (US); Shyam P. Reddy, Collegeville, PA (US)

(73) Assignee: Philadelphia Health & Education Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/462,401

(22) PCT Filed: Jul. 6, 1998

(86) PCT No.: PCT/US98/13963

§ 371 (c)(1), (2), (4) Date: Apr. 5, 2000

(87) PCT Pub. No.: WO99/02715

PCT Pub. Date: Jan. 21, 1999

(65) Prior Publication Data

US 2002/0031785 A1 Mar. 14, 2002

Related U.S. Application Data

(60) Provisional application No. 60/082,715, filed on Apr. 23, 1998, and provisional application No. 60/052,154, filed on Jul. 10, 1997.

(51) Int. Cl.$^7$ ............... G01N 33/53; C12N 1/20; C12N 5/00; C12N 15/00; C07K 1/00
(52) U.S. Cl. .............. 435/7.2; 536/23.5; 530/350; 435/320.1; 435/325; 435/252.3
(58) Field of Search ............... 435/7.21, 320.1, 435/252.3, 325; 536/23.5; 530/350

(56) References Cited

PUBLICATIONS

Wilson et al Oncogone 14(1): 1–16, See p. 2, col. 2, lines 12–16 of first full paragraph; and Fig. 1, panels, a–c on p. 3; p. 8, col. 2, lines 1–6 of second full paragraph; and Fig 5, panel b, on p. 9, Jan. 1997.*

Lu et al Cancer Research 56(20): 4578–4581, See abstract; p. 4579, col. 2, lines 14–24 of second full paragraph; Fig. 3, panels c and d on p. 4580; and p. 4581, col. 1, lines 1–8 of second full paragraph, Oct. 1996.*

Cui, et al., "Differential transcriptional activation by the N–terminal region of BRCA1 splice variants BRCA1a and BRCA1b", *Oncology Reports* 1998, vol. 5 No. 3; 585–589.

Stoppa–Lyonnet et al., "BRCA1 sequence variants in 160 individuals referred to a breast/ovarian family cancer clinic", *American Journal of Human Genetics* 1997 vol. 60 No. 5; 1021–1030.

Thakur, et al., "Localization of BRCA1 and splice variant identifies the nuclear localization signal", *Molecular and Cellular Biology* 1997 vol. 14 No. 1; 1–16.

Wang, et al., "BRCA1 proteins are transported to the nucleus in the absence of serum and splice variants BRCA1a, BRCA1b are tyrosine phosphoprotein that associate with EHF, cycling and cyclic dependent kinase", *Oncogeny* 1997 vol. 15, No. 2; 143–157.

Wilson, et al., "Differential subcellular localization expression and biological toxicity of BRCA1 and the splice variant BRCA1–delta 1b", *Oncogene* 1997 vol. 14, No. 1;1–16.

* cited by examiner

Primary Examiner—Dave T. Nguyen
Assistant Examiner—Richard Schnizer
(74) Attorney, Agent, or Firm—Licata & Tyrrell P.C.

(57) ABSTRACT

Nucleic acid sequences encoding splice variants of BRCA1 are provided.

6 Claims, 2 Drawing Sheets

SEQUENCE LISTING

<160> NUMBER OF SEQ ID NOS: 2

<210> SEQ ID NO 1
<211> LENGTH: 5711
<212> TYPE: DNA
<213> ORGANISM: Homo sapien

<400> SEQUENCE: 1

```
agctcgctga gacttcctgg accccgcacc aggctgtggg gtttctcaga taactgggcc      60
cctgcgctca ggaggccttc accctctgct ctgggtaaag ttcattggaa cagaaagaaa     120
tggatttatc tgctcttcgc gttgaagaag tacaaaatgt cattaatgct atgcagaaaa     180
tcttagagtg tcccatctgt ctggagttga tcaaggaacc tgtctccaca aagtgtgacc     240
acatattttg caaattttgc atgctgaaac ttctcaacca gaagaaaggg ccttcacagt     300 gtccttatg taagaatgat ataaccaaaa ggagcctaca agaaagtacg agatttagtc      360
aacttgttga gagctattg aaaatcattt gtgcttttca gcttgacaca ggtttggagt      420
atgcaaacag ctataatttt gcaaaaaagg aaaataactc tcctgaacat ctaaaagatg     480
aagtttctat catccaaagt atgggctaca gaaaccgtgc caaaagactt ctacagagtg     540
aacccgaaaa tccttccttg caggaaacca gtctcagtgt ccaactctct aaccttggaa     600
ctgtgagaac tctgaggaca aagcagcgga tacaacctca aaagacgtct gtctacattg     660
aattgggatc tgattcttct gaagataccg ttaataaggc aacttattgc agtgtgggag     720
atcaagaatt gttacaaatc acccctcaag gaaccaggga tgaaatcagt ttggattctg     780
caaaaaaggc tgcttgtgaa ttttctgaga cggatgtaac aaatactgaa catcatcaac     840
ccagtaataa tgatttgaac accactgaga agcgtgcagc tgagaggcat ccagaaaagt     900
atcagggtag ttctgtttca aacttgcatg tggagccatg tggcacaaat actcatgcca     960
gctcattaca gcatgagaac agcagtttat tactcactaa agacagaatg aatgtagaaa    1020
aggctgaatt ctgtaataaa agcaaacagc ctggcttagc aaggagccaa cataacagat    1080
```

-continued

```
gggctggaag taaggaaaca tgtaatgata ggcggactcc cagcacagaa aaaaggtag    1140
atctgaatgc tgatcccctg tgtgagagaa agaatggaa taagcagaaa ctgccatgct    1200
cagagaatcc tagagatact gaagatgttc cttggataac actaaatagc agcattcaga    1260
aagttaatga gtggttttcc agaagtgatg aactgttagg ttctgatgac tcacatgatg    1320
gggagtctga atcaaatgcc aaagtagctg atgtattgga cgttctaaat gaggtagatg    1380
aatattctgg ttcttcagag aaaatagact tactggccag tgatcctcat gaggctttaa    1440
tatgtaaaag tgaaagagtt cactccaaat cagtagagag taatattgaa gacaaaatat    1500
ttgggaaaac ctatcggaag aaggcaagcc tccccaactt aagccatgta actgaaaatc    1560
taattatagg agcatttgtt actgagccac agataataca gagcgtccc ctcacaaata    1620
aattaaagcg taaaggaga cctacatcag gccttcatcc tgaggatttt atcaagaaag    1680
cagatttggc agttcaaaag actcctgaaa tgataaatca gggaactaac caaacggagc    1740
agaatggtca agtgatgaat attactaata gtggtcatga gaataaaaca aaaggtgatt    1800
ctattcagaa tgagaaaaat cctaacccaa tagaatcact cgaaaaagaa tctgctttca    1860
aaacgaaagc tgaacctata agcagcagta taagcaatat ggaactcgaa ttaaatatcc    1920
acaattcaaa agcacctaaa aagaataggc tgaggaggaa gtcttctacc aggcatattc    1980
atgcgcttga actagtagtc agtagaaatc taagcccacc taattgtact gaattgcaaa    2040
ttgatagttg ttctagcagt gaagagataa agaaaaaaaa gtacaaccaa atgccagtca    2100
ggcacagcag aaacctacaa ctcatggaag gtaaagaacc tgcaactgga gccaagaaga    2160
gtaacaagcc aaatgaacag acaagtaaaa gacatgacag cgatactttc ccagagctga    2220
agttaacaaa tgcacctggt tcttttacta agtgttcaaa taccagtgaa cttaaagaat    2280
ttgtcaatcc tagccttcca agagaagaaa aagaagagaa actagaaaca gttaaagtgt    2340
ctaataatgc tgaagacccc aaagatctca tgttaagtgg agaaagggtt ttgcaaactg    2400
aaagatctgt agagagtagc agtatttcat tggtacctgg tactgattat ggcactcagg    2460
aaagtatctc gttactggaa gttagcactc tagggaaggc aaaaacagaa ccaaataaat    2520
gtgtgagtca gtgtgcagca tttgaaaacc ccaagggact aattcatggt tgttccaaag    2580
ataatagaaa tgcacagaa ggctttaagt atccattggg acatgaagtt aaccacagtc    2640
gggaaacaag catagaaatg gaagaaagtg aacttgatgc tcagtatttg cagaatacat    2700
tcaaggtttc aaagcgccag tcatttgctc cgttttcaaa tccaggaaat gcagaagagg    2760
aatgtgcaac attctctgcc cactctgggt ccttaaagaa acaaagtcca aaagtcactt    2820
ttgaatgtga acaaaaggaa gaaaatcaag gaaagaatga gtctaatatc aagcctgtac    2880
agacagttaa tatcactgca ggctttcctg tggttggtca gaaagataag ccagttgata    2940
atgccaaatg tagtatcaaa ggaggctcta ggttttgtct atcatctcag ttcagaggca    3000
acgaaactgg actcattact ccaaataaac atggacttttt acaaaaccca tatcgtatac    3060
caccactttt tcccatcaag tcatttgtta aaactaaatg taagaaaaat ctgctagagg    3120
aaaactttga ggaacattca atgtcacctg aaagagaaat gggaaatgag acattccaa    3180
gtacagtgag cacaattagc cgtaataaca ttagagaaaa tgttttttaaa gaagccagct    3240
caagcaatat taatgaagta ggttccagta ctaatgaagt gggctccagt attaatgaaa    3300
taggttccag tgatgaaaac attcaagcag aactaggtag aaacagaggg ccaaaattga    3360
atgctatgct tagattaggg gttttgcaac ctgaggtcta taaacaaagt cttcctggaa    3420
gtaattgtaa gcatcctgaa ataaaaaagc aagaatatga agaagtagtt cagactgtta    3480
```

-continued

```
atacagattt ctctccatat ctgatttcag ataacttaga acagcctatg ggaagtagtc    3540
atgcatctca ggtttgttct gagacacctg atgacctgtt agatgatggt gaaataaagg    3600
aagatactag ttttgctgaa aatgacatta aggaaagttc tgctgttttt agcaaaagcg    3660
tccagaaagg agagcttagc aggagtccta gcccttcac ccatacacat ttggctcagg     3720
gttaccgaag aggggccaag aaattagagt cctcagaaga gaacttatct agtgaggatg    3780
aagagcttcc ctgcttccaa cacttgttat ttggtaaagt aaacaatata ccttctcagt    3840
ctactaggca tagcaccgtt gctaccgagt gtctgtctaa aacacagag gagaatttat     3900
tatcattgaa gaatagctta aatgactgca gtaaccaggt aatattggca aaggcatctc    3960
aggaacatca ccttagtgag gaaacaaaat gttctgctag cttgttttct tcacagtgca    4020
gtgaattgga agacttgact gcaaatacaa acacccagga tcctttcttg attggttctt    4080
ccaaacaaat gaggcatcag tctgaaagcc agggagttgg tctgagtgac aaggaattgg    4140
tttcagatga tgaagaaaga ggaacgggct tggaagaaaa taatcaagaa gagcaaagca    4200
tggattcaaa cttaggtgaa gcagcatctg ggtgtgagag tgaaacaagc gtctctgaag    4260
actgctcagg gctatcctct cagagtgaca ttttaaccac tcagcagagg gataccatgc    4320
aacataacct gataaagctc cagcaggaaa tggctgaact agaagctgtg ttagaacagc    4380
atgggagcca gccttctaac agctaccctt ccatcataag tgactcttct gcccttgagg    4440
acctgcgaaa tccagaacaa agcacatcag aaaaagcagt attaacttca cagaaaagta    4500
gtgaataccc tataagccag aatccagaag gcctttctgc tgacaagttt gaggtgtctg    4560
cagatagttc taccagtaaa aataaagaac caggagtgga aaggtcatcc ccttctaaat    4620
gcccatcatt agatgatagg tggtacatgc acagttgctc tgggagtctt cagaatagaa    4680
actacccatc tcaagaggag ctcattaagg ttgttgatgt ggaggagcaa cagctggaag    4740
agtctgggcc acacgatttg acggaaacat cttacttgcc aaggcaagat ctagagggaa    4800
ccccttacct ggaatctgga atcagcctct tctctgatga ccctgaatct gatccttctg    4860
aagacagagc cccagagtca gctcgtgttg gcaacatacc atcttcaacc tctgcattga    4920
aagttcccca attgaaagtt gcagaatctg cccagagtcc agctgctgct catactactg    4980
atactgctgg gtataatgca atggaagaaa gtgtgagcag ggagaagcca gaattgacag    5040
cttcaacaga aagggtcaac aaaagaatgt ccatggtggt gtctggcctg accccagaag    5100
aatttatgct cgtgtacaag tttgccagaa acaccacat cactttaact aatctaatta     5160
ctgaagagac tactcatgtt gttatgaaaa cagatgctga gtttgtgtgt gaacggacac    5220
tgaaatattt tctaggaatt gcgggaggaa atgggtagt tagctatttc tgggtgaccc     5280
agtctattaa agaaagaaaa atgctgaatg agcatgattt tgaagtcaga ggagatgtgg    5340
tcaatggaag aaaccaccaa ggtccaaagc gagcaagaga atcccaggac agaaagatct    5400
tcaggggggct agaaatctgt tgctatgggc ccttcaccaa catgcccaca gatcaactgg    5460
aatggatggt acagctgtgt ggtgcttctg tggtgaagga gctttcatca ttcacccttg    5520
gcacaggtgt ccacccaatt gtggttgtgc agccagatgc ctggacagag acaatggct     5580
tccatgcaat tgggcagatg tgtgaggcac ctgtggtgac ccgagagtgg gtgttggaca    5640
gtgtagcact ctaccagtgc caggagctgg acacctacct gataccccag atcccccaca    5700
gccactactg a                                                        5711
```

<210> SEQ ID NO 2

<211> LENGTH: 1863
<212> TYPE: PRT
<213> ORGANISM: Homo sapien

<400> SEQUENCE: 2

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Asp Ser His Asp
```

```
385              390              395              400

Gly Glu Ser Glu Ser Asn Ala Lys Val Ala Asp Val Leu Asp Val Leu
            405              410              415

Asn Glu Val Asp Glu Tyr Ser Gly Ser Ser Lys Ile Asp Leu Leu
            420              425              430

Ala Ser Asp Pro His Glu Ala Leu Ile Cys Lys Ser Glu Arg Val His
            435              440              445

Ser Lys Ser Val Glu Ser Asn Ile Glu Asp Lys Ile Phe Gly Lys Thr
            450              455              460

Tyr Arg Lys Lys Ala Ser Leu Pro Asn Leu Ser His Val Thr Glu Asn
465              470              475              480

Leu Ile Ile Gly Ala Phe Val Thr Glu Pro Gln Ile Ile Gln Glu Arg
                485              490              495

Pro Leu Thr Asn Lys Leu Lys Arg Lys Arg Pro Thr Ser Gly Leu
            500              505              510

His Pro Glu Asp Phe Ile Lys Lys Ala Asp Leu Ala Val Gln Lys Thr
            515              520              525

Pro Glu Met Ile Asn Gln Gly Thr Asn Gln Thr Glu Gln Asn Gly Gln
            530              535              540

Val Met Asn Ile Thr Asn Ser Gly His Glu Asn Lys Thr Lys Gly Asp
545              550              555              560

Ser Ile Gln Asn Glu Lys Asn Pro Asn Pro Ile Glu Ser Leu Glu Lys
                565              570              575

Glu Ser Ala Phe Lys Thr Lys Ala Glu Pro Ile Ser Ser Ser Ile Ser
                580              585              590

Asn Met Glu Leu Glu Leu Asn Ile His Asn Ser Lys Ala Pro Lys Lys
            595              600              605

Asn Arg Leu Arg Arg Lys Ser Ser Thr Arg His Ile His Ala Leu Glu
            610              615              620

Leu Val Val Ser Arg Asn Leu Ser Pro Pro Asn Cys Thr Glu Leu Gln
625              630              635              640

Ile Asp Ser Cys Ser Ser Ser Glu Glu Ile Lys Lys Lys Lys Tyr Asn
                645              650              655

Gln Met Pro Val Arg His Ser Arg Asn Leu Gln Leu Met Glu Gly Lys
            660              665              670

Glu Pro Ala Thr Gly Ala Lys Lys Ser Asn Lys Pro Asn Glu Gln Thr
            675              680              685

Ser Lys Arg His Asp Ser Asp Thr Phe Pro Glu Leu Lys Leu Thr Asn
            690              695              700

Ala Pro Gly Ser Phe Thr Lys Cys Ser Asn Thr Ser Glu Leu Lys Glu
705              710              715              720

Phe Val Asn Pro Ser Leu Pro Arg Glu Glu Lys Glu Lys Leu Glu
            725              730              735

Thr Val Lys Val Ser Asn Asn Ala Glu Asp Pro Lys Asp Leu Met Leu
            740              745              750

Ser Gly Glu Arg Val Leu Gln Thr Glu Arg Ser Val Glu Ser Ser Ser
            755              760              765

Ile Ser Leu Val Pro Gly Thr Asp Tyr Gly Thr Gln Glu Ser Ile Ser
            770              775              780

Leu Leu Glu Val Ser Thr Leu Gly Lys Ala Lys Thr Glu Pro Asn Lys
785              790              795              800

Cys Val Ser Gln Cys Ala Ala Phe Glu Asn Pro Lys Gly Leu Ile His
                805              810              815
```

```
Gly Cys Ser Lys Asp Asn Arg Asn Asp Thr Glu Gly Phe Lys Tyr Pro
        820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
        930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
            965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu His Ser Met
            995                 1000                1005

Ser Pro Glu Arg Glu Met Gly Asn Glu Asn Ile Pro Ser Thr Val
    1010                1015                1020

Ser Thr Ile Ser Arg Asn Asn Ile Arg Glu Asn Val Phe Lys Glu
    1025                1030                1035

Ala Ser Ser Ser Asn Ile Asn Glu Val Gly Ser Ser Thr Asn Glu
    1040                1045                1050

Val Gly Ser Ser Ile Asn Glu Ile Gly Ser Ser Asp Glu Asn Ile
    1055                1060                1065

Gln Ala Glu Leu Gly Arg Asn Arg Gly Pro Lys Leu Asn Ala Met
    1070                1075                1080

Leu Arg Leu Gly Val Leu Gln Pro Glu Val Tyr Lys Gln Ser Leu
    1085                1090                1095

Pro Gly Ser Asn Cys Lys His Pro Glu Ile Lys Lys Gln Glu Tyr
    1100                1105                1110

Glu Glu Val Val Gln Thr Val Asn Thr Asp Phe Ser Pro Tyr Leu
    1115                1120                1125

Ile Ser Asp Asn Leu Glu Gln Pro Met Gly Ser Ser His Ala Ser
    1130                1135                1140

Gln Val Cys Ser Glu Thr Pro Asp Asp Leu Leu Asp Asp Gly Glu
    1145                1150                1155

Ile Lys Glu Asp Thr Ser Phe Ala Glu Asn Asp Ile Lys Glu Ser
    1160                1165                1170

Ser Ala Val Phe Ser Lys Ser Val Gln Lys Gly Glu Leu Ser Arg
    1175                1180                1185

Ser Pro Ser Pro Phe Thr His Thr His Leu Ala Gln Gly Tyr Arg
    1190                1195                1200

Arg Gly Ala Lys Lys Leu Glu Ser Ser Glu Glu Asn Leu Ser Ser
    1205                1210                1215
```

-continued

```
Glu Asp Glu Glu Leu Pro Cys Phe Gln His Leu Phe Gly Lys
    1220             1225                 1230

Val Asn Asn Ile Pro Ser Gln Ser Thr Arg His Ser Thr Val Ala
    1235             1240             1245

Thr Glu Cys Leu Ser Lys Asn Thr Glu Asn Leu Leu Ser Leu
    1250             1255                 1260

Lys Asn Ser Leu Asn Asp Cys Ser Asn Gln Val Ile Leu Ala Lys
    1265             1270             1275

Ala Ser Gln Glu His His Leu Ser Glu Glu Thr Lys Cys Ser Ala
    1280             1285                 1290

Ser Leu Phe Ser Ser Gln Cys Ser Glu Leu Glu Asp Leu Thr Ala
    1295             1300                 1305

Asn Thr Asn Thr Gln Asp Pro Phe Leu Ile Gly Ser Ser Lys Gln
    1310             1315                 1320

Met Arg His Gln Ser Glu Ser Gln Gly Val Gly Leu Ser Asp Lys
    1325             1330                 1335

Glu Leu Val Ser Asp Asp Glu Glu Arg Gly Thr Gly Leu Glu Glu
    1340             1345                 1350

Asn Asn Gln Glu Glu Gln Ser Met Asp Ser Asn Leu Gly Glu Ala
    1355             1360                 1365

Ala Ser Gly Cys Glu Ser Glu Thr Ser Val Ser Glu Asp Cys Ser
    1370             1375                 1380

Gly Leu Ser Ser Gln Ser Asp Ile Leu Thr Thr Gln Gln Arg Asp
    1385             1390                 1395

Thr Met Gln His Asn Leu Ile Lys Leu Gln Gln Glu Met Ala Glu
    1400             1405                 1410

Leu Glu Ala Val Leu Glu Gln His Gly Ser Gln Pro Ser Asn Ser
    1415             1420                 1425

Tyr Pro Ser Ile Ile Ser Asp Ser Ser Ala Leu Glu Asp Leu Arg
    1430             1435                 1440

Asn Pro Glu Gln Ser Thr Ser Glu Lys Ala Val Leu Thr Ser Gln
    1445             1450                 1455

Lys Ser Ser Glu Tyr Pro Ile Ser Gln Asn Pro Glu Gly Leu Ser
    1460             1465                 1470

Ala Asp Lys Phe Glu Val Ser Ala Asp Ser Ser Thr Ser Lys Asn
    1475             1480                 1485

Lys Glu Pro Gly Val Glu Arg Ser Ser Pro Ser Lys Cys Pro Ser
    1490             1495                 1500

Leu Asp Asp Arg Trp Tyr Met His Ser Cys Ser Gly Ser Leu Gln
    1505             1510                 1515

Asn Arg Asn Tyr Pro Ser Gln Glu Glu Leu Ile Lys Val Val Asp
    1520             1525                 1530

Val Glu Glu Gln Gln Leu Glu Glu Ser Gly Pro His Asp Leu Thr
    1535             1540                 1545

Glu Thr Ser Tyr Leu Pro Arg Gln Asp Leu Glu Gly Thr Pro Tyr
    1550             1555                 1560

Leu Glu Ser Gly Ile Ser Leu Phe Ser Asp Asp Pro Glu Ser Asp
    1565             1570                 1575

Pro Ser Glu Asp Arg Ala Pro Glu Ser Ala Arg Val Gly Asn Ile
    1580             1585                 1590

Pro Ser Ser Thr Ser Ala Leu Lys Val Pro Gln Leu Lys Val Ala
    1595             1600                 1605

Glu Ser Ala Gln Ser Pro Ala Ala Ala His Thr Thr Asp Thr Ala
```

-continued

```
         1610              1615              1620
Gly Tyr Asn Ala Met Glu Glu Ser Val Ser Arg Glu Lys Pro Glu
    1625              1630              1635

Leu Thr Ala Ser Thr Glu Arg Val Asn Lys Arg Met Ser Met Val
    1640              1645              1650

Val Ser Gly Leu Thr Pro Glu Glu Phe Met Leu Val Tyr Lys Phe
    1655              1660              1665

Ala Arg Lys His His Ile Thr Leu Thr Asn Leu Ile Thr Glu Glu
    1670              1675              1680

Thr Thr His Val Val Met Lys Thr Asp Ala Glu Phe Val Cys Glu
    1685              1690              1695

Arg Thr Leu Lys Tyr Phe Leu Gly Ile Ala Gly Gly Lys Trp Val
    1700              1705              1710

Val Ser Tyr Phe Trp Val Thr Gln Ser Ile Lys Glu Arg Lys Met
    1715              1720              1725

Leu Asn Glu His Asp Phe Glu Val Arg Gly Asp Val Val Asn Gly
    1730              1735              1740

Arg Asn His Gln Gly Pro Lys Arg Ala Arg Glu Ser Gln Asp Arg
    1745              1750              1755

Lys Ile Phe Arg Gly Leu Glu Ile Cys Cys Tyr Gly Pro Phe Thr
    1760              1765              1770

Asn Met Pro Thr Asp Gln Leu Glu Trp Met Val Gln Leu Cys Gly
    1775              1780              1785

Ala Ser Val Val Lys Glu Leu Ser Ser Phe Thr Leu Gly Thr Gly
    1790              1795              1800

Val His Pro Ile Val Val Val Gln Pro Asp Ala Trp Thr Glu Asp
    1805              1810              1815

Asn Gly Phe His Ala Ile Gly Gln Met Cys Glu Ala Pro Val Val
    1820              1825              1830

Thr Arg Glu Trp Val Leu Asp Ser Val Ala Leu Tyr Gln Cys Gln
    1835              1840              1845

Glu Leu Asp Thr Tyr Leu Ile Pro Gln Ile Pro His Ser His Tyr
    1850              1855              1860
```

SPLICE VARIANTS OF BRCA1

INTRODUCTION

This application is a 35 U.S.C. §371 of PCT/US98/01374, filed Jul. 6, 1998, which claims the benefit of priority from U.S. Provisional Application No. 60/082,715, filed Apr. 23, 1998, and U.S. Provisional Application No. 60/052,154, filed Jul. 10, 1997.

This invention was made in the course of research sponsored by the National Institutes of Health and the U.S. Army medical research. The U.S. Government may have certain rights in this invention.

BACKGROUND OF THE INVENTION

BRCA1 and BRCA2 are tumor suppression genes shown to be involved in 90% of familial breast and ovarian cancers (Miki et al. Science (1994) 266, 66–71). The full length gene sequence of BRCA1 is disclosed by Miki et al. and depicted herein as SEQ ID NO:1. The full length gene sequence of BRCA2 is deposited in GenBank, Accession Number U43746. Mutations in the breast and ovarian cancer susceptibility gene, BRCA1, account for about half of the inherited breast and ovarian cancers (Miki et al. (1994) Science, 266, 66–71; Easton et al. (1995) *Am. J. Hum. Genet.*, 56, 265–271; Ford et al. (1995) *Am. J. Hum. Genet.*, 57, 1457–1462) and about 10% of the sporadic ovarian cancers (Futreal et al. (1994) Science, 266, 12–122; Hosking et al. (1995) *Nature Genet.*, 9, 343–344; Merajver et al. (1995) *Nature Genet.*, 9, 439–443). BRCA2 was found to be associated more frequently with male breast cancer compared to BRCA1 (Wooster, R. et al. 1994. *Nature* 265:2088–2090. Patients with BRCA2 mutations were also found to be at higher risk for a variety of other cancers including carcinomas of the pancreas, prostate, and colon (Thorlacius, S. et al. 1996. *Nat. Genet.* 13:117–119; Phelan, C. M. et al. 1996. *Nat. Genet.* 13:120–122; Gudmundsson, J. et al. 1995. *Cancer Res.* 55:4830–4832; Tonin, P. et al. 1995. *J. Med. Genet.* 32:982–984).

The BRCA1 cDNA codes for a 1863 amino acid protein with an amino terminal zinc ring finger domain and a carboxy terminal acidic region (Miki et al. 1994 *Science*, 266, 66–71) typical of several transcriptional factors. The BRCA2 gene is composed of 27 exons and encodes a protein of 3418 amino acids with no significant homology to any known protein (Wooster, R. et al. 1995. *Nature* 378:789–792; Bork, P. et al. 1996. *Nat. Genet.* 13:22–23). Recently, the C terminal region of BRCA1 was shown to activate transcription in a heterologous GAL-4 system (Chapman, M. S. and Verma, I. M. (1996) *Nature*, 382, 678–679; Monteiro et al. (1996) *Proc. Natl. Acad. Sci. USA*, 93, 13595–13599). Murine BRCA1 has been cloned and the developmental patterns of expression studied (Lane et al. (1995) *Genes and Development*, 9, 2712–2722; Marquis et al. (1995) *Nature Genetics*, 11 17–26; Abel et al. (1995) *Hum. Molec. Genet.*, 4, 2265–2273; Sharan et al. (1995) *Hum. Mol. Gen.*, 4, 2275–2278). Expression was found to be high in rapidly proliferating tissues (Lane et al. (1995) *Genes and Development*, 9, 2712–2722; Marquis et al. (1995) *Nature Genetics*, 11 17–26), particularly those undergoing differentiation, thus suggesting a role for BRCA1 in cellular growth and differentiation. The BRCA1 gene product has been shown to be a nuclear phosphoprotein (Chen et al. (1995) *Science*, 270, 789–791; Rao et al. (1996) *Oncogene*, 12, 523–528; Scully et al. (1996) *Science*, 272, 123–125) that, when overexpressed in breast and ovarian cancer cells, results in growth inhibition in vitro and in vivo.

Conversely, inhibition of BRCA1 expression by antisense RNA in mouse fibroblasts or by antisense oligonucleotides in breast cancer cells resulted in transformation of mouse fibroblasts as well as an increase in the rate of growth of breast cancer cells (Thompson et al. (1995) *Nature Genetics*, 9, 444–450; Rao et al. (1996) *Oncogene*, 12, 523–528).

Two new alternately spliced BRCA1 transcripts referred to as BRCA1a and BRCA1b have recently been isolated and mouse fibroblast cell lines and human breast cancer cell lines expressing BRCA1a proteins have been developed (Shao et al. (1996) *Oncogene*, 13, 1–7). Overexpression of BRCA1a was found to induce apoptosis in NIH3T3 and MCF-7 cells after calcium ionophore treatment thus indicating that BRCA1 proteins, specifically BRCA1a, play a role in the regulation of apoptosis (Shao et al. (1996) *Oncogene*, 13, 1–7). The role of BRCA2 in apoptosis remains to be elucidated.

Two proteins, BARD1 and Rad51 which are human homologs of bacterial Rec A, were shown to interact both in vitro and in vivo with BRCA1 and BRCA2 indicating a role for BRCA1 proteins in tumor suppression and a role for BRCA1 in the control of recombination and genomic integrity, as well as a role for BRCA2 in DNA repair (Wu et al. (1996) *Nat. Genetics*, 14, 430–447; Scully et al. (1997) *Cell*, 88, 265–275; Sharan, S. K. et al. 1997. *Nature* 386:804–810; Zhang, H- T. et al. 1998. *Cell.* 92:433–436).

Previously, the BRCA1 gene product was shown to be localized in the nucleus (Chen et al. (1995) *Science*, 270, 789–791; Rao et al. (1996) *Oncogene*, 12, 523–528). However, differences regarding the size and subcellular localization of BRCA1 have been reported (Chen et al. (1995) *Science*, 270, 789–791; Chen et al. (1996) *Science*, 272, 125–126; Jensen et al. (1996) *Nature Genetics*, 12, 303–308; Scully et al. (1996) *Science*, 272, 123–125; Thakur et al. (1997) *Mol. Cell. Biol.*, 17, 444–452; Wilson et al. (1997) *Oncogene*, 14, 1–16). Two additional BRCA1 splice variants, BRCA1Δ672–4092 (which lacks exon 11) and BRCA1Δ11b (which lacks a majority of exon 11) were recently found to localize to the cytoplasm by immunostaining (Thakur et al. (1997) *Mol. Cell. Biol.*, 17, 444–452; Wilson et al. (1997) *Oncogene*, 14, 1–16). BRCA1Δ11b was also found to be present in significant quantities in the nuclear fractions on immunoblotting analysis.

Both BRCA1 and BRCA2 gene products have been reported to be regulated in a cell cycle-dependent manner and to have a potential transactivation function (Rajan, J. V. et al. 1996. *Proc. Natl. Acad. Sci. USA* 93:13078–13083; Vaughn et al. (1996) *Cancer Res.* 56, 4590–4594; Chapman, M. S. and I. M. Verma. 1996. *Nature* 382:678–679; Monteiro, N. A. et al. 1996. *Proc. Natl. Acad. Sci. USA* 93:13595–13599; Milner, J. et al. 1997. *Nature* 386:772–773; Cui, J. et al. 1998 *Oncology Reports* 5:585–589).

SUMMARY OF THE INVENTION

The sequences of BRCA1a and BRCA1b, two splice variants of BRCA1, have now been determined. It has been found that BRCA1a lacks a majority of exon 11 (amino acids 263–1365) while and BRCA1b lacks exons 9, 10 and a majority of exon 11 (amino acids 263–1365). Like BRCA1, BRCA1a encodes a phosphoprotein containing phosphotyrosine that associates via its amino-terminal zinc ring finger domain with E2F transcriptional factors, cyclin and cyclin dependent kinase (cdk) complexes. The amino-terminal region of BRCA1a has now been demonstrated to function as a transactivation domain when fused to heterologous GAL4 DNA binding domain. Additional studies indicate the presence of a negative regulatory domain at the carboxy-terminal regions of BRCA1 and BRCA1a proteins. It is believed that mutations in the zinc ring domain found in patients with breast and ovarian cancer may impair this activity, thus indicating that a loss of transcriptional activation by BRCA1 may lead to the development of breast and ovarian cancers.

The protein encoded by the BRCA1b splice variant, however, has now been found to have lost a portion of the amino-terminal transactivation domain as a result of alternate splicing. Accordingly, it is believed that BRCA1b may function as a dominant-negative regulator of the transcriptional activation function of BRCA1/BRCA1a proteins.

BRCA1 encoded proteins have now been found to accumulate in the cytoplasm in the presence of serum and in the nucleus in the absence of serum thus indicating that the nuclear localization of BRCA1 may be regulated by external stimuli, phosphorylation or protein—protein interactions. Like BRCA1, proteins encoded by BRCA1a and BRCA1b both act as tumor suppressors, thus indicating that exon 11 is not need for this function. Proteins which interact with BRCA1 have also been identified.

It has also been found that the amino terminal region of BRCA2, like BRCA1, associates with transcriptional factor E2F, cyclin and cdk's. BRCA2 has also been found to undergo differential splicing. The sequence of a BRCA2 splice variant, BRCA2a, has now been determined and contains a deletion of a putative transcriptional activation domain, giving rise to a protein with potential dominant negative pathophysiology. In addition, experiments examining the transcriptional factor function of BRCA2 demonstrate that the BRCA2 proteins have intrinsic histone acetyl transferase activity, activity that maps to the amino-terminal region of BRCA2. The BRCA2 proteins acetylate mainly H3 and H4 of free histones.

BRIEF DESCRIPTION OF THE FIGURES

FIG. 1 shows the structure of the splice variants BRCA1a and BRCA1b. "BNT" is used to designate the transactivation domain at the amino-terminal region, while "BID" is used to designate the inhibitory domain at the carboxy-terminal region of the protein.

FIG. 2 shows the structure of the splice variant BRCA2a.

DETAILED DESCRIPTION OF THE INVENTION

Figure 1:
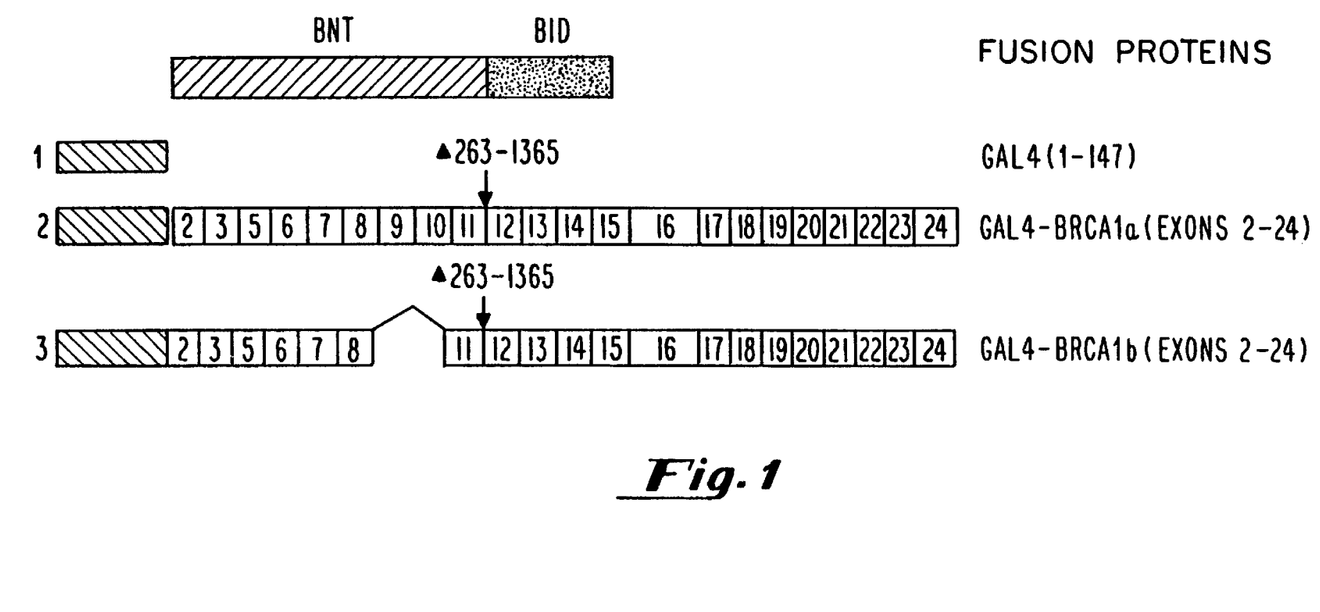

BRCA1 gene products are nuclear tyrosine phosphoproteins that have now been found to translocate to the nucleus in the absence of serum. These phosphoproteins associate in vitro with E2F transcriptional factors, cyclins and cdk complexes. The structure and nucleotide sequences of two splice variants of BRCA1, BRCA1a and BRCA1b (FIG. 1) have now been determined and the activity of proteins encoded thereby analyzed.

Full length cDNAs and several amino and carboxy-terminal deletions of BRCA1a and BRCA1b were subcloned in-frame with the GAL4 DNA binding domain vector (Webster et al. *Cell* (1988) 52, 169–178). The GAL4 fusion constructs were co-transfected in NIH3T3 fibroblast cells, along with the reporter plasmid 17MX2-tk-CAT that contains two GAL4 binding sites linked to the chloramphenicol acetyltransferase gene (CAT) and an internal control plasmid CH1210. Both full length GAL4-BRCA1a and GAL4-BRCA1b plasmids failed to show CAT activity when compared to the GAL4 vector control. Two carboxy-terminal truncated BRCA1a plasmids, one lacking exons 21–24 and the other lacking exons 16–24, failed to show transactivation. Further carboxy-terminal deletion of BRCA1a (deletion of amino acids 263–1863) but not BRCA1b plasmid (deletion of amino acids 263–1863) showed approximately 7–10 fold CAT activity. Further carboxy-terminal deletions of exons 9 and 10 of BRCA1a and exons 9 and 10 alone when fused to the GAL4 DNA binding domain failed to show significant activity thus indicating that additional sequences N-terminal and C-terminal to this region are required for transcriptional activation.

Thus, like BRCA1, the protein encoded by the BRCA1a splice variant has a transactivation domain which include the intact zinc ring finger domain at the amino-terminal regions. This domain has been shown to interact both in vitro and in vivo with BARD1 and in vitro with E2Fs, cyclins and cdk complexes and thus is important in mediating protein—protein interactions. A negative regulatory domain at the carboxy-terminal regions of both BRCA1 and BRCA1a proteins was also identified.

The BRCA1 zinc ring finger domain is the location of some of the most frequently occurring mutations linked to breast and ovarian cancers. For example, one of the BRCA1 mutations contains a frame shift in exon 2 (188 del 111; Miki et al. (1994) *Science*, 266, 66–71) which removes the zinc ring finger domain from the protein. The 185 del AG mutation, which is the most common BRCA1 mutation seen to date that occurs in 1 in 100 Ashkenazi Jewish individuals disrupts the BRCA1 gene product at the first residue of the $C_3HC_4$ domain (Shattuck-Eiden et al. (1995) *JAMA*, 15, 535–541). These frequent missense mutations Cys 61, Gly, Cys 64, Gly, and Cys 64 Tyr also disrupt the zinc ring finger domain structure. The lack of, or impaired binding of, the disrupted BRCA1 protein to E2F, cyclins and/or cdk's in patients with mutations in the zinc ring finger domain is believed to result in a loss of transcriptional activation by BRCA1, thus depriving the cell of an important mechanism for regulating cell proliferation and leading to the development of breast or ovarian cancer.

The protein encoded by the BRCA1b splice variant has also lost a portion of the amino-terminal transactivation domain as a result of alternate splicing. It is believed that the BRCA1b protein may function as a dominant-negative regulator of the transcriptional activation function of BRCA1/BRCA1a proteins. The subcellular localization of BRCA1a and BRCA1b proteins has now been determined using FLAG epitope tagged CMV promoter vectors. Data using immunofluorescence and immunoblotting analysis indicate cytoplasmic and nuclear localization of FLAG BRCA1a and FLAG BRCA1b proteins. In these experiments, the normal function of the BRCA1 protein was examined with polyclonal antibodies generated against different regions of the human BRCA1 protein. The subcellular distribution of BRCA1 in normal human mammary epithelial cell Hs578 Bst and several human breast cancer cell lines HBL-100, CAL-51, MDA MB-453, T-47D, BT-474, CAMA-1 and ZR 75-1 was determined by immunohistochemistry and immunofluorescence staining. BRCA1 was detected mainly in the cytoplasm with weak nuclear staining of normal breast epithelial cell Hs 578 Bst and several breast tumor cell lines HBL-100, MDA MB-453, T-47D, BT474, CAMA-1 and ZR 75-1. One cell line, CAL-51, which was originally obtained from a patient with invasive adenocarcinoma with extensive intraductal involvement (Gioanni et al. (1990) *Br. J. Cancer*, 62, 8–13), contained three distinct populations of cells, some in which BRCA1 was localized in the cytoplasm, some in the perinucleus and some in the nucleus.

The subcellular distribution of BRCA1 in two ovarian carcinoma cell lines NIH:OVCAR-3 and SK-OV-3 was also determined. In NIH:OVCAR-3 cells BRCA1 was localized mainly to the cytoplasm and in SK-OV-3 BRCA1 was localized mainly in the nucleus. The subcellular distribution of BRCA1 in several normal and tumor cells was also determined. BRCA1 was found to be distributed mainly in the cytoplasm of NIH3T3 mouse fibroblast cells and Saos-2 cells, both in the cytoplasm and nucleus of BRCA1a transfected NIH3T3 cells, HeLa, Colo 320, A431 and PC12 cells and mainly in the nucleus with weak cytoplasmic staining of BALB/3T3 cells. All these results suggested variable, subcellular distribution of BRCA1 proteins. These results were obtained using different BRCA1 antibodies. To determine whether the differences in the subcellular localization of BRCA1 resulted from splice mutations, differentially spliced human BRCA1 cDNA were subcloned. BRCA1a was inserted into the pFLAG-CMV-2 expression vector (Eastman Kodak Company, Rochester, N.Y.) which contains a FLAG epitope-tag sequence at the N-terminal thus allowing detection of BRCA1a protein with the use of FLAG antibody. When transfected into COS cells the FLAG BRCA1a protein was found to be localized mainly in the cytoplasm with weak nuclear staining. Subcellular fractionation of the transfected COS cells into total and nuclear fractions followed by Western blot analysis using the same FLAG antibody revealed two polypeptides migrating at 105–110 kD mainly in the cytoplasm with a small fraction of the total BRCA1a protein in the nuclear fractions. These results suggest BRCA1a p110 to be a localized both in the cytoplasm and nucleus. The doublet protein bands observed are believed to represent hyper and hypophosphorylated forms of BRCA1a proteins, similar to the 220 kDa BRCA1 protein (Chen et al. (1996) *Cancer Res.* 56, 3168–3172). Western blot analysis of FLAG immunoprecipitates obtained from p-FLAG-CMV-2-BRCA1a transfected COS cells using phosphotyrosine antibodies revealed BRCA1a to be a phosphoprotein containing tyrosine which migrated with mobility similar to an endogenous BRCA1 tyrosine phosphorylated band seen in HL60 cells. These results indicate that BRCA1a is an ≈110 kD phosphoprotein which contains tyrosine. Similarly, BRCA1b was found to be a phosphoprotein phosphorylated on tyrosine migrating with a molecular weight of ≈100 Kd.

The subcellular distribution of FLAG-BRCA1a in breast cancer cell line CAL-51 was determined by immunofluorescence analysis following transfection of pFLAG-CMV-2 BRCA1a plasmid into these cells. BRCA1a protein was observed to be distributed both in the cytoplasm as well as in the nucleus, but the cytoplasmic staining appeared to be much stronger compared to the weak nuclear staining.

To determine whether the nuclear localization of BRCA1 is dependent on the proliferation state of the cell, the subcellular distribution of BRCA1 in asynchronous and serum deprived NIH3T3 cells was determined using immunofluorescence and immunohistochemical methods with BRCA1-specific antibodies. In asynchronous serum fed NIH3T3 cells, BRCA1 was found to be localized predominantly in the cytoplasm with weak nuclear staining. In contrast, in serum starved quiescent cells most of the BRCA1 was found to be localized in the nucleus with little cytoplasmic staining. On prolonged incubation in serum free media for 48–72 hours the staining was mostly nuclear with typical nuclear dot like pattern. When the cells were refed with 10% serum for 24 hours the BRCA1 protein was found to relocate back to the cytoplasm with weak nuclear staining similar to the situation seen in asynchronous serum fed NIH3T3 cells. The same results were obtained using four different antibodies specific to different regions of BRCA1 protein, thus ruling out the possibility that nuclear BRCA1 immunofluorescence might be an artifact due to starvation. The DNA content of these cells was determined simultaneously in the presence and absence of serum by FACS analysis to give a measure of the relative percentage of G1, S, G2/M cells in each sample. Based upon these experiments, it appears that nuclear transport of BRCA1 is not cell cycle dependent and occurs irrespective of the cell cycle state. Instead, BRCA1 protein accumulates in the nucleus in the absence of serum and in the cytoplasm in the presence of serum, in NIH3T3 cells. Additional experiments were performed wherein cells were arrested in the G1 phase of the cell cycle using drugs such as aphidicolin, mimosine and double thymidine block. Results from these experiments suggest that the redistribution of the BRCA1 proteins to the nucleus in drug-treated cells is not as dramatic as seen with serum starved cells.

Similar experiments were performed in asynchronous and growth arrested serum deprived normal human breast epithelial cells Hs578 Bst, breast cancer cells HBL-100, ZR-75-1, CAMA-1 and ovarian carcinoma cells NIHOVCAR-3, using BRCA1 specific polyclonal antibodies. These cell lines include only those in which BRCA1 was found to be localized to the cytoplasm in asynchronous conditions. In these experiments, BRCA1 was found to be localized mainly in the cytoplasm of serum fed asynchronous normal breast epithelial cells Hs578 Bst, breast tumor cells HBL-100, ZR-75-1, CAMA-1 and ovarian carcinoma cell line NIHOVCAR-3 and predominantly in the nucleus of growth arrested serum deprived Hs578 Bst, HBL-100, ZR-75-1 CAMA-1 and ovarian carcinoma cell line NIHOVCAR-3. Thus, nuclear or cytoplasmic transport of BRCA1 does not appear to be spontaneous but rather is controlled by the extracellular environment with serum growth factors inhibiting the nuclear transport of the BRCA1 protein.

Two cellular proteins (p65 BIP, p32 BIP) that specifically interact with BRCA1 were detected and isolated. A fusion protein that contains GST and the zinc ring finger domain of BRCA1 (residues 1–76) was expressed in bacteria using the Gex 2T expression vector system. In order to detect cellular proteins that interact with GST-BRCA1 fusion protein, whole cell lysates of human breast cancer cells ZR-75-1 or CA1-51 metabolically labeled with [$^{35}$S] methionine were incubated with either GST or the GST-BRCA1 fusion protein immobilized on glutathione-agarose beads (GSH-beads). The beads were washed, lysed in SDS sample buffer and subjected to SDS-PAGE. SDS-PAGE analysis of the bound complex revealed bands with relative molecular weight of ≈32 kD and ≈65 kD which bound exclusively to the GST-BRCA1 fusion protein and not to GST. These bands were consistently detected in ZR-75-1, CAL-51 and HL 60 cell lysates and were designated as p65 BIP and p32 BIP respectively.

Using Western blot analysis, both p65 BIP and p32 BIP were found to bind strongly to BRCA1 even under stringent conditions without any mediating proteins. In these experiments, the BIP complexes prepared from CAL-51 cell extract separated on SDS-PAGE, transferred onto a nitrocellulose membrane, and probed with $^{32}$P-labeled GST-TK-BRCA1 fusion protein. Since GST-TK-BRCA1 contains a consensus phosphorylation site for protein kinase C at the amino terminal end, the purified protein can be $^{32}$P-labeled by an in vitro protein kinase reaction. GST-BRCA1 bound to both p65 BIP and p32 BIP unlike GST protein.

The distribution of BRCA1-binding protein in various cell lines was determined in metabolically labeled promyelocytic cell line HL 60, breast cancer cell lines ZR-75-1 and CAL-51 cells by the GST-pull down assay. Both p65 BIP and p32 BIP were detected in all cell lysates examined, although at variable levels suggesting the ubiquitous expression of p65 BIP and p32 BIP.

BIP complexes obtained from CAL-51 cells were immunoblotted with a phosphotyrosine antibody. A band corresponding to p32 was detected indicating that p32 BIP contains phosphotyrosine, a characteristic specific to cyclin associated protein kinases.

BRCA1 was also found to similarly associate with E2F cyclins and cdk's. Cell lysates obtained from CAL-51 cells were incubated with GST-immobilized on GSH-beads and BRCA1 fusion protein conjugated GSH-beads. The beads were then washed and heated in SDS sample buffer. The BIP complexes were resolved on SDS-polyacrylamide gels, transferred to nitrocellulose membrane and probed with antibodies specific to cdc2, cdk2, cdk3, cdk4, cdk5, cdk6, cyclin A, cyclin B1, cyclin D1, cyclin E, E2F-1, E2F-2, E2F-3, E2F-4 and E2F-5. The BIP complexes were recognized by antibodies specific to cdc2, cdk-2, cdk-4, cyclin D1, cyclin A, cyclin B1 and E2F-4, but not to cdk3, cdk-5, cdk-6, cyclin E, E2F-1, E2F-2, E2F-3 and E2F-5 thus indicating that BRCA1 associates with cyclin A, D1 and B1, cdc2, cdk-2, cdk-4, and E2F-4, but not with cdk3, cdk-5, cdk-6, cyclin E, E2F-1, E2F-2 and E2F-5. BRCA1 immunoprecipitates from CAL-51 cells were tested for kinase activity. These immunocomplexes show histone H1 kinase activity confirming the association of BRCA1 with cyclins/cdk complexes.

To examine the binding of cyclin A, cyclin B1, cyclin D1, E2F-1 and E2F-4 with BRCA1a and BRCA1b in vitro, cDNA sequences encoding BRCA1a and BRCA1b were inserted into pcDNA3 expression vectors. In vitro transcription and translation of BRCA1a and BRCA1b in the presence of [$^{35}$S] methionine generated radiolabeled BRCA1a and BRCA1b polypeptides of approximately 110 and 100 kD respectively. These radiolabeled proteins were passed through GST-cyclin A, GST-cyclin B1, GST-cyclin D1, GST-E2F-1, GST-E2F-4 and GST respectively. Both in vitro translated BRCA1a and BRCA1b specifically bind to GST-cyclin A, GST-cyclin B1, GST-cyclin D1, GST-E2F-1 and GST E2F-4 unlike GST alone. However, the BRCA1a splice variant bound at a reduced level compared to BRCA1b to all these different proteins. Further GST and GST E2F-1 fusion proteins were subjected to far Western Blot analysis using $^{32}$P-labeled amino-terminal BRCA1 (GST-BRCA1a amino acids 1–76, numbering from first ATG codon) fusion protein. The GST E2F-1 fusion protein band hybridized specifically to BRCA1. To further confirm the results, a fragment of BRCA1 encoding the amino-terminal 182 amino acids (amino acids 1–182) was in vitro translated and assayed for binding to GST-E2F-1 protein. The BRCA1 polypeptides bound specifically to GST-E2F-1. In a reciprocal assay, the full length human E2F-1 CDNA was in vitro translated and assayed for binding to GST-BRCA1 zinc ring finger domain fusion protein (amino acids 1–76). The E2F-1 polypeptide bound very weakly to GST BRCA1. These results suggest that the amino-terminal 76 amino acids of BRCA1 were sufficient to provide specific association with E2F-1.

Similarly, human cdc2, cdk2, cdk4 and cdk5 were in vitro translated. The proteins thus generated were assayed separately for binding to GST and GST-BRCA1(amino acids 1–76) fusion proteins. GST-BRCA1 specifically bound to cdc2 and cdk2 but not to cdk4 and cdk5 thus indicating that BRCA1 zinc ring finger domain can interact directly with cdc2 and cdk2.

Accordingly, as demonstrated herein, proteins encoded by the BRCA1a and BRCA1b splice variants have a number of similar characteristics and activities related to the tumor suppressor protein BRCA1. However, the shorter length of the nucleotide sequences of these splice variants renders them more suitable for establishing permanent cell lines for expression of these tumor suppression genes. Such cells lines will serve as useful model systems for studying BRCA1 gene therapy in breast and ovarian cancer cells. Since BRCA1a induces apoptosis of breast cancer cells, these cells lines will also be useful in studying whether the rate of apoptosis increases significantly and leaves the cancer cells more susceptible to treatment with radiation and chemotherapeutic agents such as Taxol, cisplatin, etc. These cell lines will also be useful for understanding the chain of events and identifying downstream targets through which the BRCA1 proteins turn on cellular apoptosis.

Further, the shorter length of these splice variants makes inclusion of these nucleotide sequences into viral vectors such as retroviruses for use as gene therapy agents more feasible. Viral vectors containing a splice variant of the BRCA1 tumor suppressor gene, BRCA1a can be administered to a patient suffering from breast or ovarian cancer to increase levels of protein encoded by the nucleotide sequences thereby suppressing the tumor, or inhibiting proliferation or inducing apoptosis of breast or ovarian cancer cells.

Figure 2:
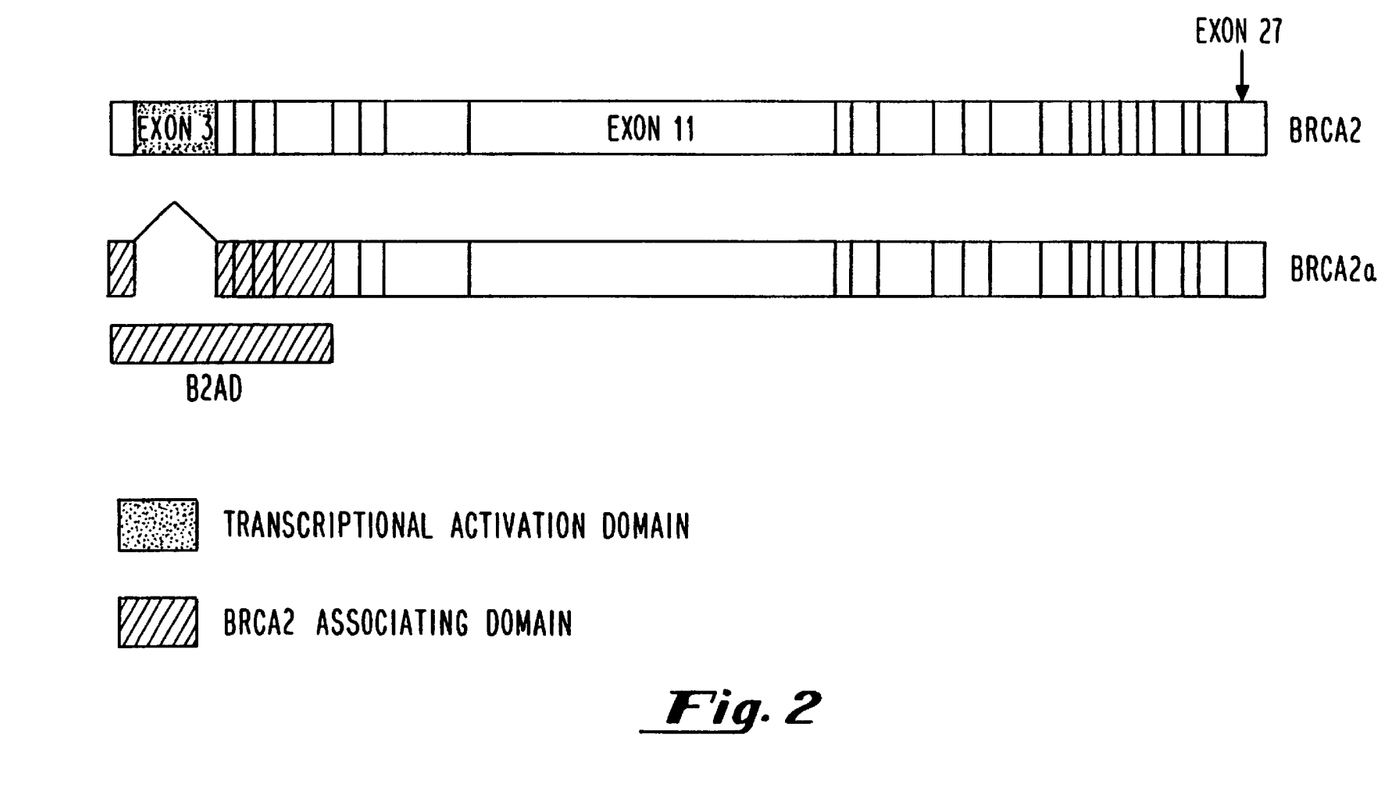

A splice variant of BRCA2, BRAC2a, has also been cloned and characterized (FIG. 2). The amino terminal region of BRCA2, like BRCA1, was shown to associate with transcriptional factor E2F, cyclins and cdk's. Thus, it is believed that proteins encoded by the tumor suppression genes BRCA1 and BRCA2 interact with E2Fs and regulate cell proliferation. The protein encoded by BRCA2a, however, has lost the transcriptional activation domain and is believed to compete with native BRCA2 in terms of DNA binding or interaction with other transcriptional factors resulting in a dominant negative effect on the transcription activation function of BRCA2.

The function of the BRCA2 tumor suppression gene was examined by cloning several cDNAs by RT-PCR and characterizing these CDNA by nucleotide sequence and restriction map analysis. It was found that one of the cDNAs (referred to herein as BRCA2a) showed alternate splicing resulting in the deletion of exon 3. Previously, this exon was shown to contain a potential transcriptional activation domain thus suggesting that BRCA2 may function as a transcription activator (Milner et al. (1997) *Nature* 386, 772–773). Since BRCA2a has lost the transcriptional activation domain, it is believed to compete with native BRCA2 in terms of DNA binding or interaction with other transcriptional factors resulting in a dominant negative effect on the transcription activation function of BRCA2. Similar dominant negative variants have been observed in other transcriptional activators (Foulkes et al. (1991) *Cell* 64, 739–749).

Further, in GST-pulldown assays, in vitro translated [$^{35}$S]-methionine labelled BRCA2 (aa 1–500) was bound to GST-cyclin A, GST-cyclin B1, GST-cyclin DA and GST-E2F-1, but not GST itself. These results indicate that BRCA2, like BRCA1, associates with E2F-1, cyclin B1 and cyclin D1, thereby negatively regulating the cell cycle. The ability of the alternatively spliced variant, BRCA2a to bind to these regulatory factors was also tested. BRCA2a was found to also bind to GST-cyclin A, GST-cyclin B1, GST-cyclin D1 and GST-E2F-1, indicating that exon 3 is not needed for these interactions. Deletion analysis was therefore performed. It was found that amino acids 1–18 and 105–272 are required for interaction with these factors. The binding of BRCA2 and BRCA2a with cyclin dependent kinases was also tested using a GST-pulldown assay. BRCA2 and BRCA2a associated with cdc2 and cdk5.

Purified recombinant proteins of BRCA2 and BRCA2a were also assayed for histone acetyl transferase activity. This was done because recent studies of several enzymes involved in acetylation and deacetylation of histone residues have revealed a potential relationship between gene transcriptional activation and histone acetylation (Brownell, J. E. et al. 1996. *Cell* 84:843–851; Parthun, M. R. et al. 1996. *Cell* 87:85–94; Yang, X. J. et al. 1996. *Nature* 382:319–324; Orgyzko, V. V. et al. 1996. *Cell* 87:953–959; Mizzen, C. A. et al. 1996. *Cell* 87:1261–1270; Roth, S. Y. and C. D. Allis. 1996. *Cell* 87:5–8; Wade, P. A. and A. P. Wolfe. 1997. *Curr. Biol.* 7:R82–R84; Pazin, M. J. and J. Kadonaga. 1997. *Cell.* 89:325–328; Wolffe, A. P. 1997. *Nature* 387:16–17). The transcriptional activators operate by disrupting the nucleosomal structure through acetylation of histones, leading to activation of gene expression. In the present experiments, the amino terminal domain of both BRCA2 and BRCA2a demonstrated histone acetyl transferase activity. Control samples, where BRCA2 or BRCA2a was replaced with bovine serum albumin (BSA), showed no significant histone acetyltransferase activity. Similar control experiments where histones were replaced by BSA (lysine rich nonhistone protein) also failed to show significant acetyltransferase activity. These data show for the first time that BRCA2 proteins exhibit specific acetyl transferase activity to histones. Therefore, BRCA2 can be termed a histone acetyl transferase.

Since the amino terminal region of BRCA2 and BRCA2a show the histone acetyltransferase activity, it is likely that exon 3 (amino acids 18–105) which is responsible for the transactivation function of BRCA2 is not needed for histone acetyltransferase function. These data indicate that the transactivation and histone acetyltransferase functional domains of BRCA2 do not overlap with each other. In order to determine which histones are acetylated by BRCA2 proteins, the histone acetyltransferase assay was performed using free core histones and then analyzed the resulting products by SDS-polyacrylamide gel electrophoresis followed by fluorography. The results show that BRCA2 proteins acetylated primarily H3 and H4 of free histones. These results were confirmed using free histones.

The in vivo histone acetyltransferase activity of BRCA2 was then examined. Immunoprecipitation of BRCA2 from whole cell extracts was tested for acteyltransferase activity. Results demonstrated that immunoprecipitated BRCA2 carries acetylase activity specific for histones. Considered together with the in vitro data, the results support the finding that BRCA2 has intrinsic histone acetyltransferase activity, and may provide the mechanism for activation of gene expression. Patients with mutations in histone acetyltransferase or transactivation domains of BRCA2 would show a loss of gene expression which is critical for growth inhibition and differentiation, resulting in a subset of familial breast and ovarian cancers.

As with BRCA1a and BRCA1b, the shorter length of the BRCA2a splice variant makes it useful in establishing permanent cell lines for expression of this tumor suppression gene. Such cell lines will be useful model systems for studying BRCA2 gene therapy in breast, ovarian and prostate cancer cells.

Further, as with BRCA1b, the presence of this dominant negative variant, BRCA2a, may result in the dysfunction of the tumor suppressor protein BRCA2. Thus, these proteins may serve as a marker for identifying individuals with greater potential for developing breast, ovarian and prostate cancer. Altered levels of BRCA1a may also serve as a prognostic and/or diagnostic tool for breast and ovarian cancer.

Levels of the splice variants BRCA1a, BRCA1b and BRCA2a, can be routinely determined by one of skill in the art in accordance with well known methods. For example, tissue or blood samples can be screened for the presence of these splice variants by PCR, RT-PCR, Western blotting or protein truncation assays.

Several critical growth regulators like the product of the pRB, a tumor suppressor protein have been shown to associate with E2F-both in vitro and in vivo resulting in net inhibition of E2F-mediated transactivation and E2F release from pRB is an important event in the activation of genes required for S-phase entry (Weinberg, R. A. (1995) *Cell,* 81, 323–330). Accordingly, in vitro associations of BRCA1 and BRCA2 and splice variants thereof with E2F demonstrated herein are expected to correlate in similar fashion with in vivo activity.

The following nonlimiting examples are provided to further illustrate the present invention.

EXAMPLES

Example 1

Cell Lines

NIH3T3 cells and their derivatives, MCF-7, MDA-MB-453 and A431 cells were grown at 37° C. in DMEM supplemented with 10% fetal bovine serum (FBS), 1% penicillin-streptomycin (PS); HS578 Bst cells were grown in DMEM supplemented with 10% FBS, 1% PS and 30 ηg/ml EGF, CAL-51 cells were grown in DMEM containing 10% FBS, 1% PS, 0.6 $\mu$g/ml bovine insulin, $5\times10^{-3}$ $\mu$g/ml transferrin and 146 mg/Liter glutamine; ZR 75-1 and COLO 320 were grown in RPMI 1640 supplemented with 10% FBS, 1% PS and 10 $\mu$g/ml bovine insulin; NIH:OVCAR-3 cells were cultured in RPMI 1640 supplemented with 20% FBS, 1% PS and 10 $\mu$g/ml bovine insulin; PC12 cells were grown in RPMI 1640 supplemented with 10% horse serum and 5% FBS, 1% PS; SK-OV-3 and HBL 100 cells were grown in McCoy's 5a medium supplemented with 10% FBS and 1% PS; Saos-2 cells were grown in McCoy's 5a medium supplemented with 15% FBS and 1% PS; CAMA-1 cells were cultured in Eagle's Minimum Essential Medium (MEM) supplemented with 10% FBS and 1% PS. All the cell lines except CAL-51 cells were obtained from The American Type Culture Collection (Rockville, Md.). CAL-51 cells were originally obtained from a patient with invasive adenocarcinoma with extensive intraductal involvement as described by Gioanni et al. (1990) *Br. J. Cancer,* 62, 8–13.

Example 2

Immunohistochemistry

The different cell lines in the logarithmic stage of growth cultured in chamber slides were made quiescent in the presence of DMEM only for a period of 24–72 hours. Cells were then washed in PBS and subjected to immunohistochemistry analysis using rabbit anti BRCA1 carboxyterminal or an amino terminal peptide antibody (Santa Cruz Biotechnology Inc., Santa Cruz, Calif.), rabbit polyclonal antibody generated against GST fusion proteins containing amino acids 1 to 76 and amino acids 1 to 331 of the BRCA1 protein in accordance with procedures described by Rao et al. (1996) *Oncogene*, 12, 523–528.

Example 3

Plasmid Construction and Transfections

BRCA1a cDNA and BRCA1b cDNA were subcloned into pFLAG-CMV vector (Eastman Kodak Company, Rochester, N.Y.) by PCR. Purified DNA, 5 µg for chamber slides and 20 µg for 100 mm petri dishes of pFLAG-CMV-2 expression vector or pFLAG-CMV-2 expression vector containing the BRCA1a cDNA, were transfected into COS and CAL-51 cells using the Invitrogen kit according to the manufacturer's recommendations (Invitrogen Corp., San Diego, Calif.). After 48–72 hours post transfection cells were processed for immunofluorescence analysis or the cell extracts were subjected to Western blot analysis using FLAG M2 antibody (Eastman Kodak Company, Rochester, N.Y.) in accordance with procedures described by Rao et al. (1996) *Oncogene*, 12, 523–528.

Example 4

Immunofluorescence

Immunofluorescence analysis was performed using pFLAG-CMV-2 BRCA1a transfected COS and CAL-51 cells cultured in chamber slides and fixed in 3.7% formaldehyde at room temperature. Slides were washed in PBS and PBS with 0.05% Triton X-100 and blocked in blocking solution (4% normal goat serum, 0.05% Triton x-100 in PBS) for 10 minutes at room temperature. The cells were incubated with primary anti FLAG M2 antibody diluted 1:100 for COS and CAL-51 cells, then washed three times with PBS, blocked with blocking solution for an additional 10 minutes at room temperature followed by incubation with the secondary antibody (FITC conjugated goat anti mouse IgG). After rinsing in PBS, the slides were mounted with mounting media and photographed on a confocal microscope.

Example 5

Preparation of Total Nuclear Extract and Western Blot Analysis

COS cells were harvested 48 hours post transfection by washing in PBS and treating with trypsin. For preparing total cell extracts, the cells were lysed in RIPA buffer and the lysate was centrifuged at 14,000 rpm for 30 minutes at 40° C. The supernatant was assayed for protein concentration by Bradford's method (Bio-Rad) and ≈50–100 µg of protein was subjected to Western blot analysis in accordance with procedures described by Rao et al. (1996) *Oncogene*, 12, 523–528. The nuclear extract was prepared in accordance with procedures described by Hurst et al. (1990) *Molecular and Cellular Biology*, 10, 6192–6203. In accordance with these procedures, cells were lysed in nuclear extract buffer 1 and centrifuged at high speed for 1 minute at room temperature. The crude nucleus was suspended in nuclear extract buffer II. Nuclear debris was removed by centrifugation for 1 minute at room temperature. The supernatant was diluted by the addition of 20 mM Hepes (pH 7.4). The protein concentrations were determined by Bradford's method (Bio-Rad) and ≈50–100 µg of protein was subjected to Western blot analysis.

For Western blotting analysis ≈50–100 µg of cell/nuclear extract in SDS sample buffer were loaded on a 10% SDS-PAGE in Bio-Rad mini-protean II cell as described previously by Rao et al. (1996) *Oncogene*, 12, 523–528. After electro transfer onto PVDF membrane, the FLAG-BRCA1a fusion protein was detected with anti-FLAG M2 antibody diluted 1:100 using Western exposure chemiluminescent detection system from Clonetech or ECL.

Example 6

Metabolic Labeling of Cells

Confluent 100 mm plates of HL 60-cells were labeled with $^{32}$P-orthophosphoric for 4 hours. The cells were lysed in radioimmunoprecipitation assay buffer. Following sedimentation the supernatants were subjected to immunoprecipitation using rabbit anti BRCA1 peptide or recombinant protein antibody or preimmune serum in accordance with procedures described by Rao et al. (1996) *Oncogene*, 12, 523–528. The samples were subjected to 10% SDS polyacrylamide gel electrophoresis and autoradiography. In some cases the cold HL60 cell lysates were subjected to immunoprecipitation using carboxyterminal BRCA1 peptide antibody and then subjected to Western blot analysis using phosphotyrosine antibody (Santa Cruz Biotechnology).

Example 7

Expression and Purification of GST Fusion Protein

Log phase cultures of *E. coli* BL21 (DE3) LysS transformed with the pGEX 2TK-BRCA1 (aa 1–76), pGEX2T-BRCA1 (aa 1–76), pGex 2T-E2F-1, pGex2T-CycA, pGEX2T-cycB1, pGEX2T-cycD1, pGEX2T-E2F-4 plasmids were incubated with IPTG for 3 hours. The cells were pelleted in STE buffer containing 100 µg/ml lysozyme, 5 mM DTT, 1 mM PMSF and 2% Sarkosyl, sonicated on ice and centrifuged at 10,000 g for 10 minutes. Triton X-100 was added to the supernatant and applied to a glutathione sepharose 4B column (Pharmacia Biotech, Uppsala, Sweden) and the GST-BRCA1 or GST-cyclins or GST-E2F fusion proteins were either left immobilized or eluted with elution buffer containing glutathione. The GST-BRCA1 fusion proteins were labeled with $^{32}$P in a 100 µl final volume containing 20 mM Tris (pH 7.5), 100 mM NaCl, 12 mM $MgCl_2$, 10 µCi of ($-^{32}$P) ATP, 1 µg GST-fusion protein and 100 units of cAMP dependent protein kinase (Sigma Chemical Co., St. Louis, Mo.) on ice for 30 minutes.

Example 8

GST Pull Down Assay

CAL-51, ZR 75-1 or HL 60 cells were labeled with $^{35}$S-methionine in accordance with procedures described by Rao et al. (1996) *Oncogene*, 12, 523–528. The cells were washed in cold phosphate buffered saline (PBS) and scrapped into 1 ml of TNN buffer (Takashima et al. (1994) *Oncogene*, 9, 2135–2144) and lysed by rotating for 30 minutes at 4° C. The lysates were centrifuged at 14,000 g for 30 minutes and subjected to protein binding assay as described by Takashima et al. (1994) *Oncogene*, 9, 2135–2144. For protein binding assay cell extracts were precleared overnight with GSH-beads and then incubated with either GST protein-conjugated GSH-beads or GST-BRCA1 (containing residue 1 to 76 of the BRCA1a protein). Proteins were incubated with GSH beads for 2 hours at 4° C. The beads were then washed in TNN buffer and boiled in SDS sample buffer and loaded on a 10% SDS PAGE. The gels were fixed, treated with enhance, dried and exposed to X-ray films. For in vitro binding experiments 10–20 µl of full length in vitro translated BRCA1a, BRCA1b, BRCA1 (amino acids 1–182), cdc2, cdk2, cdk4, cdk5 and E2F-1 were tested for binding to GST-E2F-1 or GST-E2F-4.

Example 9

Immunoprecipitation and In Vitro Kinase Assays

CAL-51 cells were lysed in 1 ml TNN buffer and immunoprecipitated with recombinant BRCA1 polyclonal antibody (amino acid 1–76) as described previously by Rao et al. (1996) *Oncogene*, 12, 523–528. The immunoprecipitates were washed in kinase buffer and measured for kinase activity toward histone H1 in accordance with procedures described by Makela et al. (1994) *Nature*, 371, 254–257.

Example 10

Far Western Blot Analysis

Far Western blot analysis was performed. After transfer the nitrocellulose membrane was washed in 1× HBB buffer (Singh et al. (1989) *Biotechniques*, 7, 252–261) and treated sequentially with 1× HBB buffer containing different concentrations of guanidine HCl ranging in concentration from 6 M to 0.19 M. The membrane was hybridized in Hyb 75 buffer (Kaelin et al., 1992) containing 0.1 mM $ZnCl_2$ and $^{32}P$-labeled GST-TK-BRCA1 protein ($10^6$ cpm/ml) overnight at 4° C. Subsequently, the membrane was washed in Hyb 75 buffer, air dried and exposed to X-ray film.

Example 11

Histone Acetyl Transferase Activity Assay

The histone acetyltransferase activity (HAT) assay was carried out as described by Bannister and Kouzarides (1996. *Nature* 384:641–643) with slight modifications. Briefly, Crude core histones (15 µg) and GST-fusion proteins of BRCA2 and BRCA2a (50–100 ng) were mixed to give a final volume of 30 µl in buffer IPH (50 mM Tris-HCl, pH 8.0, 150 mM NaCl, 5 mM EDTA, 0.5% by volume NP-40, 0.1 mM PMSF). Reactions were initiated by the addition of [$^3H$]-acetyl CoA and the reactions incubated at 3° C. for 10 to 45 minutes. Incorporation of the radiolabeled acetyl groups into histones was determined by liquid scintillation counting of reactions spotted onto P-81 Whatman filters.

What is claimed is:

1. An isolated nucleic acid sequence encoding human BRCA1a or BRCA1b, wherein the isolated nucleic acid sequence encoding human BRCA1a consists of bases 1–788 and 4096–5711 of human SEQ ID NO:1 and wherein the isolated nucleic acid sequence encoding BRCA1b consists of bases 1–665 and 4096–5711 of human SEQ ID NO:1.

2. The isolated protein encoded by the nucleic acid sequence of claim 1.

3. A vector comprising the nucleic acid sequence of claim 1.

4. A host cell transfected with the vector of claim 3.

5. An in vitro method of identifying agents capable of modulating an amount or a selected activity of human BRCA1a protein comprising contacting cells expressing the human BRCA1a protein of claim 2 with an agent suspected of modulating the protein level or the selected activity of said BRCA1a protein and measuring the level or the selected activity of the human BRCA1a protein of claim 2 in the cells.

6. An in vitro method of identifying agents capable of modulating an amount of human BRCA1b protein comprising contacting cells expressing the human BRCA1b protein of claim 2 with an agent suspected of modulating the protein level and measuring the level of the human BRCA1b protein of claim 2 in the cells.

* * * * *